(12) United States Patent
Knox

(10) Patent No.: US 6,197,060 B1
(45) Date of Patent: Mar. 6, 2001

(54) OTOLOGIC PROSTHESES

(75) Inventor: Glenn W. Knox, Jacksonville, FL (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 09/233,394

(22) Filed: Jan. 19, 1999

(51) Int. Cl.$^7$ .................................................. A61F 2/18
(52) U.S. Cl. ................................................................. 623/10
(58) Field of Search ................................ 623/10; 600/25

(56) References Cited

U.S. PATENT DOCUMENTS

| 3,191,188 | 6/1965 | Mercandino et al. . |
| 3,196,462 | 7/1965 | Robinson . |
| 3,711,869 | 1/1973 | Shea . |
| 3,838,468 | 10/1974 | Armstrong . |
| 3,931,648 | 1/1976 | Shea . |
| 4,292,693 | 10/1981 | Shea et al. . |
| 4,740,209 | 4/1988 | Gersdorff . |
| 4,957,507 | * 9/1990 | Lenkauskas ............................ 623/10 |
| 5,171,240 | 12/1992 | Hanwong . |
| 5,370,689 | 12/1994 | Causse . |
| 5,433,749 | 7/1995 | Clifford . |
| 5,514,177 | * 5/1996 | Kurz et al. ............................ 623/10 |

FOREIGN PATENT DOCUMENTS

| 0 379 470 | 8/1990 | (EP) . |
| 0 909 554 | 4/1999 | (EP) . |
| WO98 22042 | 5/1998 | (WO) . |
| WO98 24371 | 6/1998 | (WO) . |

OTHER PUBLICATIONS

Database WPI, Section PQ, Week 9207, Derwent Publications Limited, London, GB; Class P32, AN 92–054843 XP002136222 & SU 1 634 272A (Tomsk Univ.Sibe. Phys.), Mar. 15, 1991 abstract.

Fujihiko Kasano et al., "Utilization of nickel–titanium shape memory alloy for stapes prosthesis", Auris Nasus Larynx, vol. 24, pp. 137–142 (1997).

* cited by examiner

Primary Examiner—David J. Isabella
(74) Attorney, Agent, or Firm—Fish & Richardson P.C.

(57) ABSTRACT

Otologic protheses of shape-memory metal alloy self-secure about an otologic structure when heat is applied to a preformed bight by means of a laser.

14 Claims, 2 Drawing Sheets

OTOLOGIC PROSTHESES

FIELD OF THE INVENTION

The present invention relates generally to otologic prostheses; and more particularly, to a novel and improved otologic prosthesis for relieving impaired conductive hearing of the middle ear.

BACKGROUND OF THE INVENTION

Otosclerosis is a common cause of progressive conductive hearing loss in which softening and hardening of minute areas of the ossicles (malleus, incus and stapes) in the middle ear produce abnormal bone growth and impede conduction of sound vibration from the eardrum to the inner ear. In about ten percent of patients with otosclerosis, the bone growth spreads to the stapes bone in particular, the final link in the middle ear chain. The stapes is a small stirrups-shaped bone with its base resting in a small groove, commonly called the oval window, in intimate contact with the inner ear fluids. When the amount of otosclerosis at this location is significant, as determined by careful hearing tests, a stapedectomy (or stapedotomy) is the treatment of choice.

A stapedectomy is a microsurgical technique in which all or a portion of the stapes is replaced by a prosthesis. When the procedure was first introduced in the 1950s, many surgeons became skilled in the technique and while it is now performed by many more surgeons, on an average, there are relatively few performed per surgeon. Hence, proficiency is harder to maintain for the occasional stapes surgeon.

A stapedectomy is usually performed through an incision in the ear canal under local or general anesthesia. A flap consisting of canal skin and the tympanic membrane (eardrum) is elevated and the posterior superior bony external auditory canal is drilled away to expose the stapes, incus, and chorda tympani (facial nerve). The ossicles are palpated to confirm fixation of the stapes and mobility of the malleus and incus.

With care taken to preserve the chorda tympani, the joint between the incus and the stapes is separated with a knife, and a laser or other microsurgical instrument severs the stapes tendon and one crus (leg) of the stapes. The arch of the stapes bone may then be removed by fracturing off the other crus allowing the footplate to remain in the oval window. A laser is next employed to form a minuscule hole in the footplate for posting the stapedial prosthesis. In some cases, the footplate is also removed by a so-called "large hole" technique and a vein grafted to the internal wall of the tympanum to cover the opening and to support the prosthesis.

After a hole is made in the footplate (or tissue is placed over the opening to the inner ear made after removing the footplate) one end of a biocompatible plastic or metal piston-like stapedial prosthesis of proper length is posted in the hole and the other end attached to the incus. A piece of fat or other tissue is taken, such as from a small incision behind the ear lobe, to seal any hole in the window, and the eardrum is folded back into its normal position with a small gelatin sponge to hold it in position.

A critical part of the procedure is attaching the prosthesis around the lenticular process of the incus due to its minuteness and delicate nature, typically about 3.5 mm to 6 mm long and 0.6 mm to 0.8 mm diameter, For instance, in U.S. Pat. No. 5,370,689 to Causse one end of the prosthesis fabricated of PTFE is posted in a hole drilled in the exposed footplate and a split eyelet at the other end must be crimped around the incus. In U.S. Pat. No. 3,714,869 to Shay Jr. one end of the prosthesis is placed on a vein graft invaginated into the oval window, and a split eyelet at the other end must be forced open by elastic deformation to fit onto the incus. Elastic recovery capacity of the eyelet causes it to restore to its original form in about 20 minutes and grip the incus firmly. U.S. Pat. No. 3,838,468 to Armstrong discloses a stapedial prosthesis for use in cases where the footplate is also removed. A piston is fixed at one end to a vein graft for covering the oval window. A wire of stainless steel, platinum, gold or like biocompatible material shaped like a shepherd's crook extending from the other end, is crimped about the lenticular process of the incus. U.S. Pat. No. 5,433,749 to Clifford et al. discloses a stapedial prosthesis of metal or plastic in which one end of a piston extends into the fluid in the inner ear and the other end is secured to the incus by a separate heat-shrinkable sleeve when heat is applied as by a laser.

It is readily apparent that great care and skill are required to secure these and similar prostheses to the lenticular process of the incus. The minute size of the prostheses also makes them extremely difficult to manipulate into proper position for tightening around the incus, even with state-of-the-art microsurgical instrumentation. Once in place, if the prosthesis is not tightened sufficiently about the incus, fluctuating hearing loss, dizziness, or extrusion of the prosthesis may occur. If it is too tight, necrosis of the incus may occur. In either case, the tightening procedure in itself may cause trauma to the delicate middle ear structures, including fracture or subluxation (dislocation) of the incus.

Other otologic protheses may be implanted by similar procedures directly between the malleus and the footplate of the stapes or the oval window of the inner ear.

OBJECTS OF THE INVENTION

With the foregoing in mind, it is an object of the present invention to provide an otologic prosthesis which can be installed more easily with more confidence by the occasional ossicle replacement surgeon and with fewer complications and better hearing results.

Another object is to provide an otologic prosthesis which can be more readily connected to an ossicle with much less trauma to the delicate middle ear structures.

Still another object is to provide a stapedial prosthesis which is relatively simple in construction, utilizes state-of-the-art materials, and which can be more easily manipulated in the middle ear.

SUMMARY OF THE INVENTION

More specifically, these and other objects and advantages of the invention are accomplished by an otologic prosthesis of biocompatible shape memory alloy for conducting sound vibration from the eardrum, through the inner ear, to the oval window of the inner ear. One embodiment of the invention is a stapedial prosthesis including a shaft of nickel-titanium wire having means on one end portion for posting in a hole formed in the footplate of the stapes. The other end portion of the shaft, in a thermoelastic martensitic phase, is reversely turned to form a bight, as manufactured, to fit snugly around the lenticular process of the incus when installed. The bight is plastically deformable at ambient temperatures to fit loosely against the incus. When the wire temperature is elevated to a higher temperature, as by application of a laser beam, the bight returns to its memorized shape for positively embracing the incus. Preferably, a heat sink flange is mounted on the shaft for conducting heat to the bight when the laser energy is applied. Other embodiments of prostheses are disclosed.

BRIEF DESCRIPTION OF THE DRAWINGS

The foregoing and other objects, features and advantages of the present invention should become apparent from the following drawings, in which.

DESCRIPTION OF THE PREFERRED EMBODIMENTS

Figure 1:
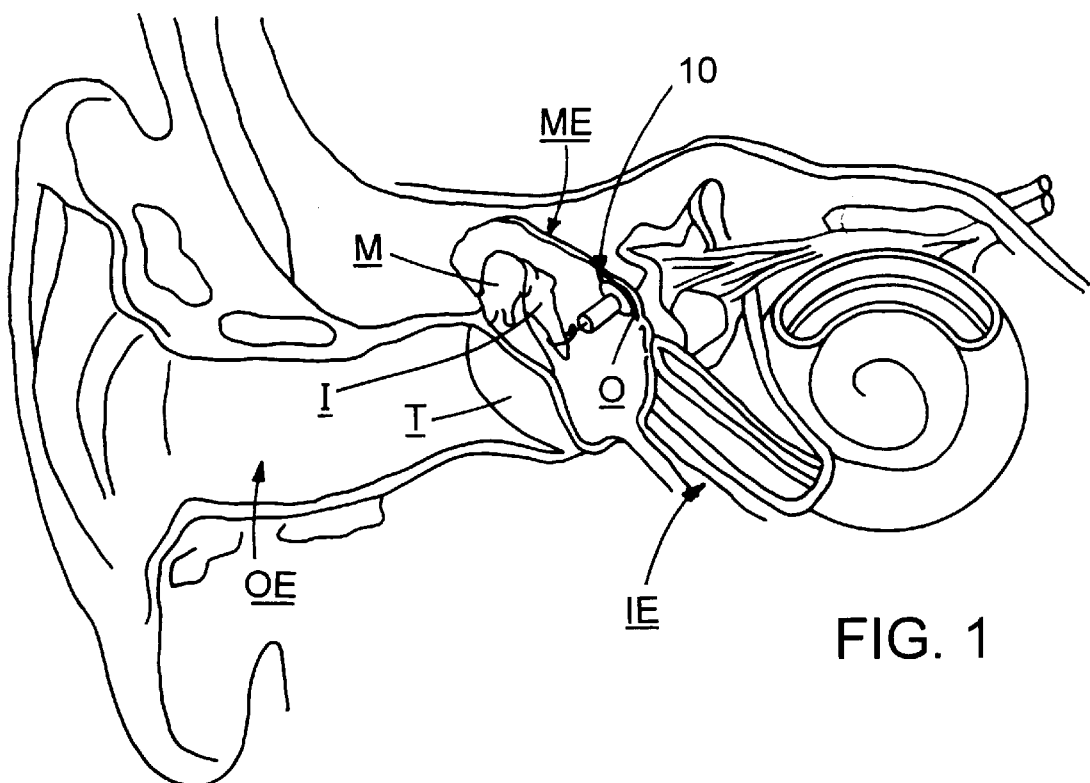
FIG. 1 is an enlarged, fragmentary, partially broken-away, perspective view of a human ear having one embodiment of an otologic prosthesis according to the present invention.

Referring now to the drawings, FIG. 1 illustrates a human ear having an outer ear structure OE, a middle ear structure ME, and an inner ear structure IE. The middle ear ME is separated from the outer ear OE by the tympanic membrane T. The malleus M is connected to the tympanic membrane T, and the incus I is connected to the malleus. One embodiment of an otologic prosthesis 10 embodying the present invention is shown connecting the incus I to the oval window 0 adjacent the inner ear IE.

The otologic prosthesis 10 illustrated in FIG. 1 is used in a so-called stapedectomy. When installed, the otologic prosthesis 10 provides a sound-conductive connection between a first otologic structure, such as the incus process I, and a second otologic structure, such as the oval window 0. When installed as illustrated, vibrations from the incus process I are transmitted to the oval window 0 in the same manner as with a conventional prosthesis.

As discussed heretofore, a significant problem that exists with a conventional otologic prosthesis of the type described resides in the connection of the outer end of the prosthesis to the incus process. Presently, it is necessary to crimp the outer end of a wire-form prosthesis about the incus process, and because it requires great care, it is a difficult and time consuming portion of the overall stapedectomy procedure.

According to the present invention, the problems associated with prior art otologic prostheses are overcome by the otologic prosthesis 10 which comprises an elongate shaft 11 of nickel-titanium metal wire alloy having biocompatible shape-memory properties, such as Nitinol. The shaft 11 has an upper, or outer, end portion 12 that is reversely turned on itself to form an open ended bight 13. As manufactured, the prosthesis 10 has an overall length of about 4 mm, and the reversely turned bight has a radius of approximately 0.05 mm. The diameter of the wire shaft is approximately 0.005 mm. The bight 13 is adapted to engage the incus process I as illustrated in FIG. 3D in the manner to be discussed.

Figure 2:
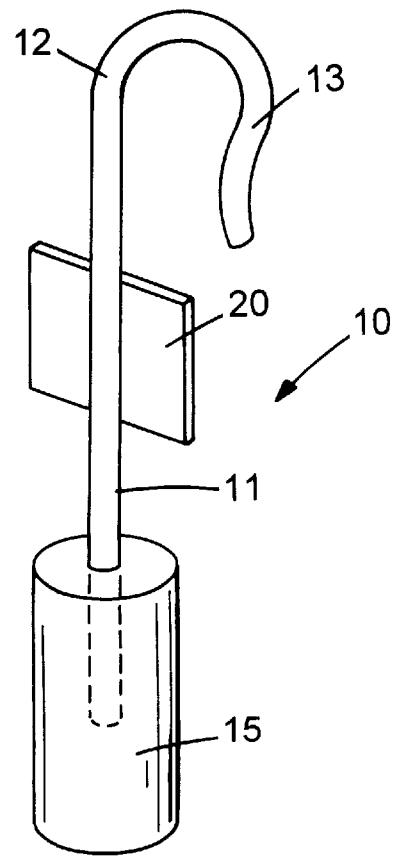
FIG. 2 is an enlarged perspective view of the otholithic prosthesis illustrated in FIG. 1.
Figure 3A:
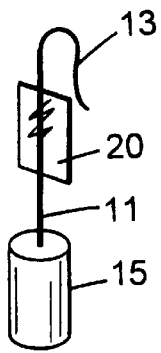
FIGS. 3A–3D are perspective views of the prosthesis embodiment of FIG. 1, but showing it in various phases of installation on an incus process.
Figure 3B:
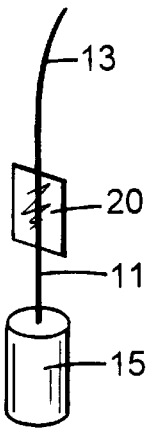
Figure 3C:
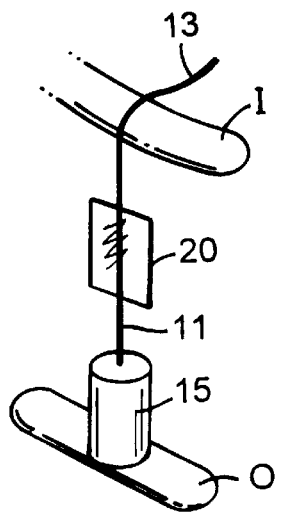
Figure 3D:
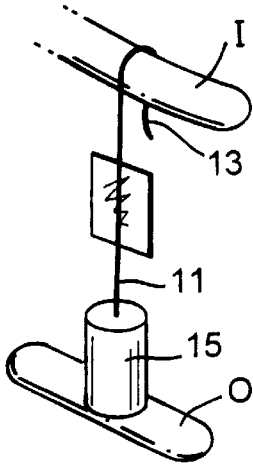

The prosthesis shaft 11 has a lower, or inner, end portion 14 remote from the bight 13, and a fastening means as provided on this end portion for securing the shaft 11 to a second otologic structure, such as the oval window O shown in FIG. 3D. In the embodiment of FIG. 2 the fastening means includes a cylindrical piston 15 of plastic, such as polytetrafluoroethylene (PTFE) molded about the lower end of the shaft 11.

The bight 13 is opened by means of a tool to receive the incus process I and self-closes in response to heat to grip it. In order to accelerate the self closing action, a heat sink flange 20 is provided on the shaft 11 between the bight 13 and the piston 15. In the illustrated embodiment, the heat sink flange 20 is provided by a flat metal plate which is preferably disposed in a plane transverse to the plane in which the bight 13 is formed, such as orthogonal to the plane of the bight 13. The heat sink flange 20 is secured to the shaft 11 as by welding. Thus, the heat sink flange 20 is disposed with its surface area readily exposed to the surgeon for receiving electromagnetic energy, such as may be applied by means of the laser beam customarily used in stapedectomys.

When struck by a laser beam, the heat sink flange 20 conducts heat upwardly along the shaft 11 to the bight 13 causing it to reversely turn on itself into its as manufactured condition for gripping the incus process as illustrated in FIG. 3D. The heat sink flange 20 is also large relative to the shaft 11 to provide a readily visible target for the surgeon to aim the laser beam.

Installation of the prosthesis 10 is straight-forward. As best seen in FIG. 2A, the prosthesis 10 is shown in its normal, as manufactured, condition as described with respect to FIG. 2. After removal from the sterile package in the operating theater, the reversely turned bight 13 is straightened as illustrated in FIG. 3B. The prosthesis 10 is installed with its piston 15 engaged with the oval window O, and the bight 13 is loosely engaged with the incus process as illustrated in FIG. 3C. Thereafter, the surgeon applies electromagnetic radiation by a laser to the heat sink flange 20 for heating the shaft 11 and causing the bight 13 to reversely turn on itself to its as manufactured shape and thereby firmly grip the incus process I. A temperature of approximately 86° F. (30° C.) is sufficient to cause the bight to reversely turn and engage the incus process I in short order. Thereafter, body temperature, being above the activation temperature, maintains the bight 13 in firm engagement with the incus process I.

Figure 4:
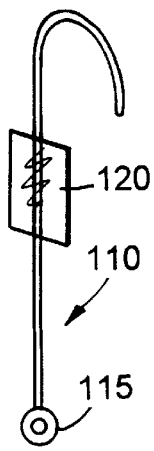
FIG. 4 is an elevational view another embodiment of an otologic prosthesis according to the present invention.

FIG. 4 illustrates a second embodiment 110 of a prosthesis of the present invention. In the embodiment of FIG. 4, the piston is replaced with a circular loop 120 formed on the bottom of the shaft as in conventional wire prostheses.

Figure 5:
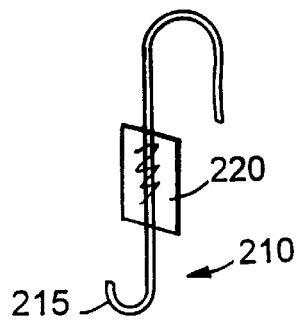
FIG. 5 is an elevational view of a further embodiment of otologic prosthesis according to the present invention.

In the embodiment of FIG. 5, a fastening means is provided by a reversely turned shaft end portion 215, much like the reversely turned upper end bight portion of the shaft illustrated in FIG. 2, but of a smaller radius. The reversely turned lower end portion in the FIG. 5 embodiment is in the same plane as the upper end bight and this embodiment is particularly suited for a malleus to stapes prosthesis.

In both the embodiments of FIG. 4 and FIG. 5, a heat sink flange 120 and 220 is provided for purposes as described above.

Figure 6:
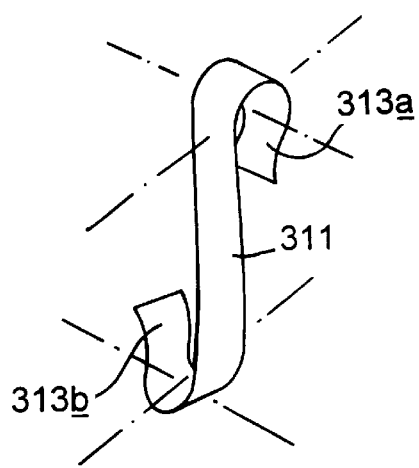
FIG. 6 is an elevational view of yet another embodiment of an otologic prosthesis according to the present invention.

In a further embodiment, illustrated in FIG. 6, the shaft 311 is not of cylindrical wire construction. Rather, it is of a flat ribbon like construction providing upper and lower bights 313a and 313b lying in planes perpendicular to each other. An advantage of this construction is that the ribbon shaft 311 provides a continuous heat sink flange. This embodiment is particularly suited for use in providing an incus to stapes prosthesis.

In view of the foregoing, it should be apparent that the present invention now provides otologic prostheses which overcome many of the limitations of prior art prostheses by eliminating the need for crimping wire about an otologic structure and the concomitant disadvantages associated therewith.

While preferred embodiments of the present invention have been described in detail, various modifications, alterations and changes may be made without departing from the spirit and scope of the present invention as defined in the appended claims.

What is claimed is:

1. A self-securing otologic prosthesis, comprising:
   an elongated shaft formed of biocompatible shape-memory alloy,
   one end of said shaft having a reversely-turned end portion forming a first bight,
   said first bight capable of being deformed for receiving a first otologic structure and upon application of heat closing into gripping engagement with said first otologic structure, and
   fastening means on an opposite end of said shaft remote from said first bight for operatively engaging a second otologic structure.

2. The self-securing otologic prosthesis according to claim 1 including a flange on said shaft providing a heat sink for enabling heat to be transferred by conduction to said first bight after engagement with said first otologic structure.

3. The self-securing otologic prosthesis according to claim 1 wherein said shaft is of small-diameter nickel-titanium metal alloy wire.

4. The self-securing otologic prosthesis according to claim 1 wherein said fastening means includes an enlarged cylindrical body.

5. The self-securing otologic prosthesis according to claim 4 wherein said cylindrical body has a circular end portion and is of a biocompatible plastic.

6. The self-securing otologic prosthesis according to claim 1 wherein said fastener means is provided by a closed loop formed integral with said shaft.

7. The self-securing otologic prosthesis according to claim 1 wherein said fastening means includes a second bight lying in a plane transverse to the plane of said first bight.

8. The self-securing otologic prosthesis according to claim 1 wherein said shaft mounts a heat sink flange in a plane transverse to the plane of the first bight for receiving electromagnetic radiation.

9. The self-securing otologic prosthesis according to claim 1 wherein said first otologic structure is an incus, said first bight is formed to attach to said incus, said second otologic structure is an oval window, and said fastening means is formed to operatively engage said window.

10. The self-securing otologic prosthesis according to claim 1 wherein said first otologic structure is an incus, said first bight is formed to attach to said incus, said second otologic structure is a stapes, and said fastening means is formed to operatively engage said stapes.

11. The self-securing prosthesis according to claim 1 wherein said first otologic structure is an incus, said first bight is formed to attach to said incus, said second otologic structure is a stapes footplate, and said fastening means is formed to operatively engage said stapes footplate.

12. The self-securing prosthesis according to claim 1 wherein said first otologic structure is a malleus, said first bight is formed to attach to said malleus, said second otologic structure is an oval window, and said fastening means is formed to operatively engage said window.

13. The self-securing otologic prosthesis according to claim 1 wherein said first otologic structure is a malleus, said first bight is formed to attach to said malleus, said second otologic structure is a stapes footplate, and said fastening means is formed to operatively engage said stapes footplate.

14. The self-securing prosthesis according to claim 1 wherein said first otologic structure is a malleus, said first bight is formed to attach to said malleus, said second otologic structure is a stapes, and said fastening means is formed to operatively engage said stapes.

* * * * *

(12) EX PARTE REEXAMINATION CERTIFICATE (7006th)
United States Patent
Knox

(10) Number: US 6,197,060 C1
(45) Certificate Issued: Aug. 18, 2009

(54) OTOLOGIC PROSTHESES

(75) Inventor: Glenn W. Knox, Jacksonville, FL (US)

(73) Assignee: The Governor and Company of the Bank of Scotland, London (GB)

Reexamination Request:
No. 90/008,649, May 10, 2007

Reexamination Certificate for:
Patent No.: 6,197,060
Issued: Mar. 6, 2001
Appl. No.: 09/233,394
Filed: Jan. 19, 1999

(51) Int. Cl.
*A61F 2/18* (2006.01)
*A61B 19/00* (2006.01)

(52) U.S. Cl. ........................................................ 623/10
(58) Field of Classification Search .................. None
See application file for complete search history.

(56) References Cited

U.S. PATENT DOCUMENTS

| | | | |
|---|---|---|---|
| 3,620,212 A | 11/1971 | Fannon | |
| 3,711,869 A | 1/1973 | Shea, Jr. | |
| 3,838,468 A | 10/1974 | Armstrong | |
| 3,868,956 A | 3/1975 | Alfidi et al. | |
| 4,233,690 A | 11/1980 | Akins | |
| 4,655,776 A | 4/1987 | Lesinski | |
| 4,740,209 A | 4/1988 | Gersdorff | |
| 5,171,240 A | 12/1992 | Hanwong | |
| 5,219,358 A | 6/1993 | Bendel et al. | |
| 5,514,178 A | 5/1996 | Torchio | |
| 5,690,671 A | 11/1997 | McGurk | |
| 5,855,577 A | 1/1999 | Murphy-Chutorian et al. | |
| 5,876,434 A | 3/1999 | Flomenblit et al. | |
| 5,989,242 A | 11/1999 | Saadat | |
| 6,066,083 A | 5/2000 | Slater et al. | |

FOREIGN PATENT DOCUMENTS

| | | |
|---|---|---|
| DE | 4210235 C1 | 11/1993 |
| EP | 0909554 | 10/1998 |
| WO | WO-A 98/24371 | 11/1998 |

OTHER PUBLICATIONS

Eviatar, Abraham, *Otologic Medicine and Surgery*, Chapter 46, "Stapes Surgery," pp. 1261–1267.
Schuknecht, Harold F., *Surgery of the Ear and Temporal Bone*, Chapter 20, Otosclerosis Surgery, pp. 223–239.
Jurgen Theissing, "HNO–Operationsletire," pp. 352, 382, George Thieme Verlag Stuttgart (1996).
Dietrich Plester et al., "Atlas der Ohrchirugie," pp. 98, 107, 108, 110, Kohlhammer Verlag Stuttgart (19890.
Hans–Georg Boenninghaus, "Hals–Nasen–Ohrenheilkunde," pp. 138, 139, Springer verlag Berlin (1996).
Enatsu, K., Utilization of Ni–Ti shape memory alloy for ossicular prosthesis and its biocompatibility with the incus of cats, Otologia Fukuoka 32, (1986) 256–269 ('Enatsu')(translation not provided).
Kasano F., Utilization of nickel–titanium shape memory alloy for stapes prosthesis, Auris Nasus Larynx 24 (1997) 137–142 ('Kasano').

*Primary Examiner*—David O. Reip

(57) ABSTRACT

Otologic protheses of shape-memory metal alloy self-secure about an otologic structure when heat is applied to a preformed bight by means of a laser.

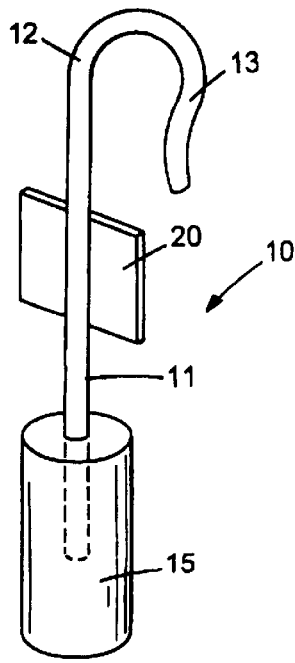

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 3–7 and 9–14 are cancelled.

New claims 15–18 are added and determined to be patentable.

Claims 2 and 8 were not reexamined.

*15. A method for implanting a self-securing otologic prosthesis between first and second otologic structures, the self-securing otologic prothesis comprising (1) an elongated shaft formed of a biocompatible shape-memory alloy, one end of the shaft having a reversely-turned end portion forming a first bight for attaching to the first otologic structure and (2) fastening means on an opposite end of the shaft remote from the first bight for operatively engaging the second otologic structure, the method comprising:*

*deforming the first bight to receive the first otologic structure; and*

*applying a laser beam to heat the elongated shaft to close the first bight into gripping engagement with the first otologic structure.*

*16. The method of claim 15 further comprising engaging the fastening means with the second otologic structure.*

*17. The method of claim 16 wherein the engaging of the fastening means with the second otologic structure occurs before deforming the first bight to receive the first otologic structure.*

*18. The method of claim 16 wherein the engaging of the fastening means with the second otologic structure occurs before applying the laser beam to heat the elongated shaft.*

\* \* \* \* \*